(12) United States Patent
Roldan et al.

(10) Patent No.: US 6,864,228 B1
(45) Date of Patent: Mar. 8, 2005

(54) USE OF BISPHOSPHONATES FOR THE TREATMENT OF OSTEOGENESIS IMPERFECTA

(75) Inventors: Emilio J. A. Roldan, Buenos Aires (AR); Anibal Perez Lloret, Buenos Aires (AR)

(73) Assignee: Gador, S.A. (AR)

( * ) Notice: Subject to any disclaimer, the term of this patent is extended or adjusted under 35 U.S.C. 154(b) by 0 days.

(21) Appl. No.: 09/570,275

(22) Filed: May 12, 2000

(51) Int. Cl.$^7$ .............................................. A61K 31/66
(52) U.S. Cl. ........................... 514/2; 514/102; 514/108
(58) Field of Search ............................ 514/2, 102, 108

(56) References Cited

U.S. PATENT DOCUMENTS 5,403,829 A * 4/1995 Lehtinen
5,409,911 A * 4/1995 Tyler

OTHER PUBLICATIONS

Glorieux, 1998, "Cyclic administration of pamidronate in children with severe osteogenesis imperfecta" New England journal of Medicine, 339 (14): pp 947–952.*
Landsmeer–Beker, 1997 "Treatment of osteogenesis imperfecta with the bisphosphonate olpadronate" Eur. J. Pediatr., 156 (10): pp. 792–794.*
Bembi, 1997 "Intravenous pamidronate treatment in osteogenesis imperfecta" J. Pediatr. 131 (4): 622–625.*
Plotkin, 2000, "Medical treatment of osteogenesis imperfecta" Drug Dev. Res. 49 (3):141–145.*

* cited by examiner

Primary Examiner—Christopher Tate
Assistant Examiner—Roy Teller
(74) Attorney, Agent, or Firm—Pendorf & Cutliff

(57) ABSTRACT

This procedure consists in the first stage, of the administration of enough quantity of bisphosphonate preparation during the necessary period of time to acquire a degree of volumetric mineral density of the cortical tissue of application, within the normal range (average IDS). Then the administration of the bisphosphonate preparation is interruption in order to enable the development of the sectional momentum of inertia. The length of the second stage can be determined by means of a tomography. That is to say, that the periods of administration or non-administration of the mineralizing agent are defined or controlled by precise osteologic variables and therefore are not fixed. If during the second stage the cortical mineral density drops by 6–10% of the maximum value previously obtained, administration of bisphosphonate preparation should be resumed until the corresponding maximum adjusted value is reached again. The proposed procedure of a period with bisphosphonate followed by another period without the bisphosphonate agent improves fracture resistance, provided that the length of both periods is controlled by defined osteologic variables.

16 Claims, 6 Drawing Sheets

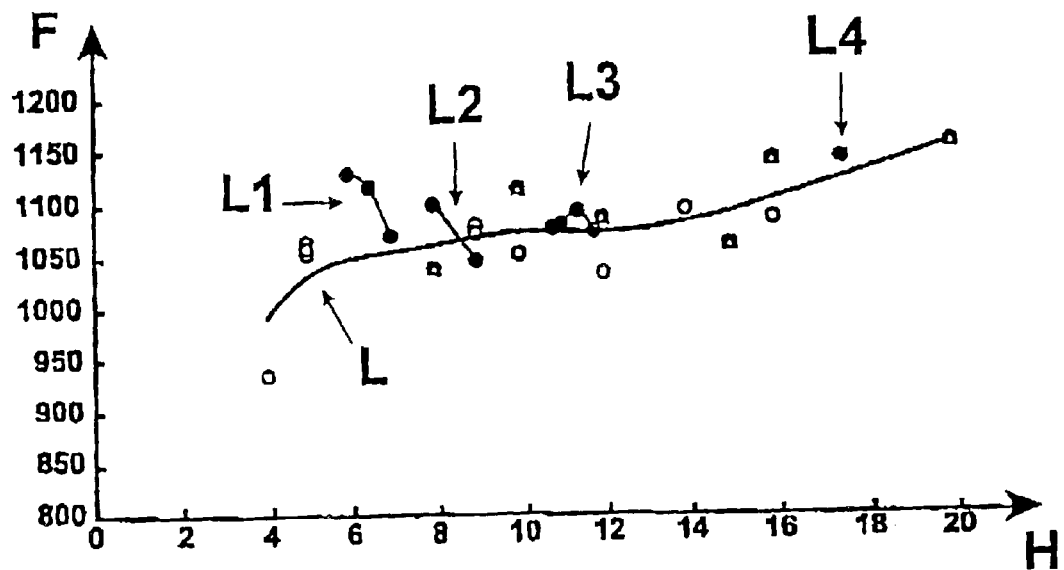
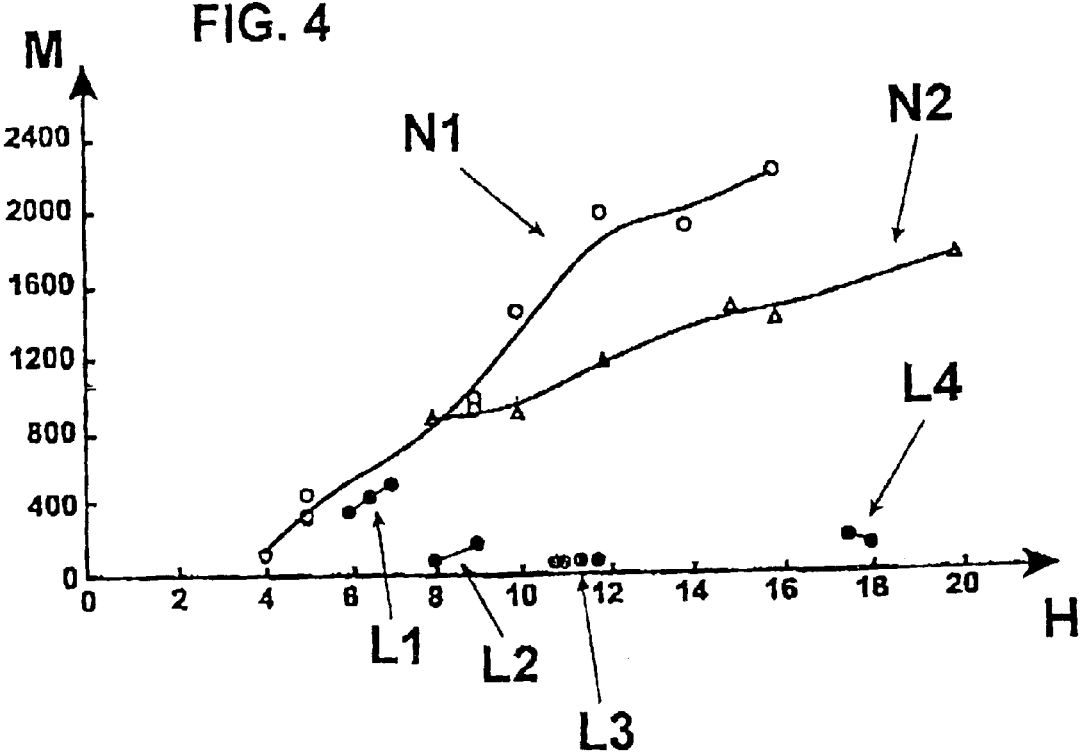

USE OF BISPHOSPHONATES FOR THE TREATMENT OF OSTEOGENESIS IMPERFECTA

BACKGROUND OF THE INVENTION

Field of the Invention

The present invention is related to the use of a bisphosphonate for the treatment of Osteogenesis imperfecta, a hereditary disease that affects the bones and which had no effective formulations and treatment until today. More particularly, the invention is related to the use of a bisphosphonate for the manufacture of a medicament for the treatment of Osteogenesis imperfecta and a kit for the treatment of Osteogenesis imperfecta.

SUMMARY OF THE INVENTION

This invention also comprises the development of simple formulations and/or products with a combined presentation in multi-packing with the purpose of providing a pharmaceutical specialty based on the procedure of the present invention.

Osteogenesis Imperfecta also known as brittle bone disease is a rare genetic disorder that affects approximately 2,000 children in Argentina and 20,000 children in the United States. It is because of its low incidence in the population that the research and development for the formulation of products and treatments are classified as "orphans". Due to the same reasons, published data are based on the experiences carried out, analyzed and studied in isolated cases, or very small groups of patients.

The "orphanage" in research for the development of effective formulations for the treatment of this disease, is more noticeable in the pharmaceutical industrial field, owing to the fact that it is difficult to recoup the finds which are needed for the industrial research and development of any method aimed at such a small number of potential users. Consequently, the development of a new formulation and the invention of a new procedure require a solid industrial protection that makes possible the investment needed to obtain a product that meets the standards of the present sanitary regulations.

Osteogenesis Imperfecta (OI) is a genetic disorder characterized by causing several bone fractures and deformities. It affects children since born hindering their normal growth and the development of their skeletons.

The children affected by Osteogenesis Imperfecta suffer multiple fractures. Some children may even be born with fracture produced during birth labour. Fractures may be caused by minimum pressure and therefore affect growth and survival.

The subsequent bone deformations may be the cause of a high extra-osseous morbidity and mortality rate, since they affect the normal functioning of vital organs such as the respiratory system and only those patients with the most benign form of the disease, have a better prospect to reach maturity. Therefore, bone development control determines these patients' prognosis. The main manifestation of this genetic defect is the synthesis of a very low quality collagen. In the bone, Collagen is the main organic component of the tissular matrix, forming a fibrous meshwork that serves as deposit and orientation of the mineral crystals. This defective bone material fosters the development of deformities and fractures.

There also exist at least two other important factors, which affect bone fragility:

I) The restoring mechanism (a humoral and cellular system which tends to renovate low-effective mineral tissue) increases bone turnover. In doing so, they worsen the calcium metabolic state, since the result of its action is Osteopenia (mineral tissue of low calcium density), fostering bone deformation.

II) The scarce muscular development hinders the main physiological stimulus for the architectural development of bones, fostering the formation of bone structures which are unsuitable to bear the daily mechanical challenges, That is to say, that bone disorder caused by Osteogenesis Imperfecta is qualitative as well as quantitative, where both the mineralization and conformation of the bone are insufficient to withstand deformations and fractures.

The disease does not currently count with an effective treatment. It is difficult to modify the genetic basis of the disorder despite the fact that gene transfer —a possibility under development has already been patented (Bonadio J., U.S. Pat. No. 5,763,416; Berg R. A., U.S. Pat No. 5,667, 839).

A different form to attenuate Osteopenia is the use of the so-called bone formation stimulators, such as fluor salts or human Interleukin 4 or its analogs.

These procedures attain a positive balance of calcium, but are not used to correct defects of bone structure and material quality. Alternatively, it has been attempted to attenuate Osteopenia (the quantitative defect of mineral density) using biphosphonates by following the procedures applied to other diseases which cause Osteopenia, such as Osteoporosis.

In this regard, it should be taken into account that biphosphonates are substances that inhibit the bone calcium metabolism, producing less negative and sometimes even positive results, increasing mineral density. Examples of known bisphosphonates are pamidronate, alendronate, olpadronate, risedronate, neridronate, ibandronate, zolendronate, IG-9402, etc.

Thus, the administration of bisphosphonates in children with Osteogenesis Imperfecta was started in very short cyclical schedules (for example, of only 2–3 months followed by a same period without treatment or of 15 days of treatment every 3 months) and in fixed schedules (of the same length for all patients).

Since the bones treated with these "fixed cyclical procedures" are under growth, treatment resulted in mineralization bands alternated with bands of Osteopenia, mainly in the areas of higher bone growth. The resulting mineralized tissue is of dubious mechanical efficiency (Devogelaer J. P. et al, Skeletal Radiol. 1987, 16: 360; Devogelaer J. P. et al., Medicina [Buenos Aires] 1997, 57 [S1]:110).

Later, the bisphosphonates were used in a different way, at small oral doses, but daily and continuously (a procedure named "continuous"). In this way, both bone resorption inhibition and an increase in total mineral density were achieved (Landsmeer-Beker E A et al., Eur. J. Pediatr. 1997, 156:792). It is not possible to assess if bone resistance to fracture improves with this procedure.

The problem underlying the present invention was thus to provide a new means and methods for the treatment of Osteogenesis imperfecta which overcomes the disadvantages of currently used therapeutic approaches.

This problem has been solved in one aspect by the use of a bisphosphonate for the manufacture of a medicament for the treatment of Osteogenesis imperfecta which is characterized insofar that the bisphosphonate is administered in a first stage and the bisphosphonate is not administered in a second stage, wherein the first stage is for obtaining a defined bone mineral density and the second stage is for architectonic expansion of the bone.

In an embodiment the defined bone mineral density is obtained when ft reaches the bone mineral density which is normal for a person of the age of the patient to be treated or when it reaches a steady state despite further application of the bisphosphonate.

In a further embodiment the defined bone mineral density is expressed as cortical mineral density, more particularly as the volumetric mineral density of the cortical tissue.

In a still further embodiment the defined bone mineral density is within the average range of a person±1 Ds wherein said person is not suffering from Osteogenesis imperfecta and is of the same age as the person suffering from Osteogenesis imperfecta to be treated.

In an additional embodiment the duration of the second stage is determined by the develops ment of the sectional momentum of inertia, In a further embodiment the duration of the second stage is determined by bone stability to torsion or flexion In a more preferred embodiment the sectional momentum of inertia and/or bone stability to torsion or flexion corresponds to the values of a person not suffering from Osteogenesis imperfecta at least one characteristic of whom, preferably the age, otherwise corresponds to the person suffering from Osteogenesis imperfecta to be treated.

In another embodiment the architectonic expansion of the bone, the bone stability to tension or flexion and/or bone mineral density is determined by a method selected from the group comprising tomography and radiologic means.

In still a further embodiment the second stage is terminated if the bone mineral density, preferably the cortical mineral density, drops by 5–10% of the maximum value obtained in the first stage.

In a more preferred embodiment a flier stage is added which corresponds to the first stage comprising administration of the bisphosphonates.

In an even more preferred embodiment subsequent to the added further stage another stage which corresponds to the second stage comprising non-administration of the bisphosphonate, follows.

In a particularly preferred embodiment at least one further cycle is added which cycle comprises a stage corresponding to the first stage comprising administration of the bisphosphonate and a stage corresponding to the second stage comprising non-administration of the bisphosphonates.

In another embodiment the bisphosphonate is selected from the group comprising pamidronate, olpadronate, amino-pamidronate, amino-olpadronate (IG 9402), amino-alendronate, amino-etidronate, alendronate, neridronate, ibandronate, risedronate, tiludronate, etidronate, clodronate, incadronate, zolendronate and mixtures thereof.

In a preferred embodiment the bisphosphonate is pamidronate or olpadronate or a mixture thereof.

In a further embodiment the bisphosphonate or mixture of bisphosphonate is a bisphosphonate preparation further comprising at least one compound selected from the group comprising pharmaceutically acceptable calcium salts, pharmaceutically acceptable fluor salts, vitamin D, PTH, fractions of PTH and other hormones.

In still a further embodiment the bisphosphonate is present in gastro-resistant formulations suitable for oral administration In another preferred embodiment the administration of bisphosphonate at 25 to 300 mg daily doses.

In an embodiment the bisphosphonate or the bisphosphonate comprising preparation is an injectable preparation, preferably the doses of bisphosphonate are from about 5–60 mg for each administration at one-week to six-months intervals.

In an additional embodiment the bisphosphonate is comprised in a preparation with tie preparation being selected from the group comprising tablets, capsules, solid forms, liquid soluble or suspension forms, gels and soft capsules.

In a further aspect the problem is solved by a kit comprising a plurality of bisphosphonate dosage forms for the treatment of Osteogenesis imperfecta.

In a preferred embodiment of the kit said kit further comprises a package insert specifying the use as in any of claims 1 to 19.

In a further aspect, the problem is solved by a procedure applicable to medical preparations of bisphosphonates and their formulation for the treatment of Osteogenesis Imperfecta characterized by the administration of enough quantity of the preparation of bisphosphonates during the necessary length of time until it is obtained a degree of volumetric mineral density of the cortical tissue within normal range (mean±1 DS) for the patient's age; the subsequent interruption of the administration of the preparation of bisphosphonate during the time in which the cortical mineral density do not drop lower than 5–10% when the cortical mineral density falls by 5–10% of the previously obtained maximum value, the resuming of the administration of bisphosphonates until the maximum value adjusted to the patient's age is reached again and so forth In a preferred embodiment the procedure is characterized by the fact that its preparation may contain more than one bisphosphonate and some of the synergic combinations formed by pharmaceutically acceptable calcium salts, pharmaceutically acceptable fluor salts, vitamin D, PTH, fractions of PTH or other hormones.

In a further embodiment the inventive procedure is characterized by the administration of bisphosphonate preparations in gastro-resistant formulations to be administered orally.

In still a further embodiment the procedure is characterized by the administration of bisphosphonates at 25 to 300 mg daily doses.

In preferred embodiment the procedure is characterized by the ft that disodium pamidronate is used as bisphosphonate.

In another preferred embodiment the procedure is characterized by the administration of injectable preparations where the doses of bisphosphonates from 5–60 mg each time, at one-week to six-month intervals.

In another embodiment of the procedure it is characterized by fact that the preparation containing bisphosphonates is included in pharmaceutical preparations (such as tablets, capsules, solid forms, liquid soluble or suspension forms, gels, and soft capsules) that can be administered by respective organic ways (oral, parenteral, intranasal, rectal or topical).

In still a further embodiment the procedure is characterized by the fact that the preparation contains olpadronate as bisphosphonate.

In another embodiment the procedure is characterized by the preparation is obtained in a box designed with combined presentation packaging.

In still a further embodiment the procedure is characterized by the fact that the preparation is obtained in a box designed with conjoint presentation packaging.

The inventors were able to determines that, by applying the above described "continuous" procedure during 2–5 years, the specific mineral density of cortical regions (outer layers of the bone)—which is considered the most critical for bone mechanical performance—is mineralized until it reaches normal values (see example 1).

At the same time, however, bone endoestal resorption inhibition (inside long bones) produced by the same bisphosphonates is so noticeable that the diaphysial structure attained has a low resistance to deformation and fracture. For example, sectional inertia momentum (a ratio between internal and external diameters of the bone structure that indicates the architectural efficiency of the section) is very low after continuous treatment with bisphosphonates. That is why the bones are so unstable in the presence of torsion and/or flexion forces, even when the defect of mineralization of the disease has been corrected.

Therefore, with the "continuous" procedure the bones arc still brittle and can be deformed (example 1). Consequently, it should be considered that higher mineralization does not mean greater bone strength.

The inventors have also noticed that shortly after discontinuing the administration of bisphosphonates to children with Osteogenesis Imperfecta that had attained a normal level of cortical mineral density, the level of mineral endoestal density in these children decreased. The outer layers also lose mineral but at a lower pace. Furthermore, parallel to the above mentioned facts, it was possible to prove that the stability of the studied diaphysial section tends to increase. This can be explained by a greater sectional momentum of inertia. (See example 2).

During the interruption in the administration of bisphosphonate, it can be seen that the bone tends to acquire resistance to fracture, although paradoxically it loses some mineral density. That is, it improves qualitatively at the expense of slight quantitative deterioration, thus resulting in a positive functional balance. This fact can be seen in those children whose growth, modeling and remodeling bone mechanisms are very operative. The same mechanisms are poorly expressed inadequately mineralized tissue, but may work better in normally mineralized tissue, at the first stage of the application of bisphosphonate.

If the administration on of bisphosphonate is interrupted for a short time, it will not take place the momentum of inertia needed to improve bone stability. If on the other hand, the period of interruption is too long, the action of the bone modulator system will not only produce Osteopenia in the tissue, but will probably affect the bone architecture. Therefore, it is essential to control the length of each period of treatment; with or without administration of bisphosphonate.

Taking into account the above mentioned observations, the inventors provide a procedure to apply bisphosphonate or a preparation comprising at least one bisphosphonates in two stages. The first stage aims at the obtention of a well-mineralized bone structure, able to respond to bone formation stimuli.

This stage is named WITH, or of MINERALIZATION, with the administration of bisphosphonates. The purpose of the second stage is to enable the architectonic expansion of the bone; for example, a greater momentum of sectional inertia This stage is called WITHOUT or of ARCHITECTURIZATION, without bisphosphonates and for a period long enough to keep, essentially, the mineral density previously achieved.

The subsequent application of both stages (WITH-WITHOUT that is to say, MINERALIZATION plus ARCHITECTURIZATION), fosters a bone which is more stable when subject to mechanical forces, thus resisting fractures. This is the innovative step of the present invention, since the architectonic variable bad never been considered before for the treatment of this disease. In this regard, an Osteopenia-producing period had neither been considered before in an approach for the treatment of Osteogenesis imperfecta. Such period is now defined and controlled by densitometric variables, which differentiates it from the previous cycle schemes, fixed and the same for all patients.

In fact, the critical aspect of the procedure is the individual determination of the optimum duration of the stages WITH/WITHOUT or of MINERALIZATION plus ARCHITECTURIZATION, since as already mentioned, the mineral and architectonic improvement do not take place at the same time, but can even counteract each other.

That is to say, that it is necessary to establish the application period of the bisphosphonates in order to mineralize the cortical bone (cortical or external resorption inhibition) without deteriorating the momentum of inertia (by internal or endoestal resorption inhibition) and the period during which it is convenient to interrupt the administration of bisphosphonate to favour the expansion of the momentum of inertia (internal osseous resorption) without a significant deterioration of the mineralization achieved in the bone. Such periods can be individually affected by several variables, including general genetic structure, the period of development of the patient, the seriousness of the disease, the available muscular mass, nourishment, physical exercising, hormonal stage, etc. Because of this, no procedures with fixed periods such as those applied in already known procedures (cyclic or continuous) can be designed, but the timing of the period should be adjusted to each patients osteologic state.

The inventor of the present procedure have determined that by applying tomographic techniques with specific sore designed to assess simultaneously mineral density and architectural variables (momentum of inertia, sectional cortical area or the so-called bone stability indexes), optimal individual timing for each of the proposed stages can be established (see examples 1 and 2).

Based on this background, the inventors provide a new procedure, the results of which enable to treat Osteogenesis Imperfecta. This procedure differs from those early known because it considers the effects of bone "mineralization" and "architecturization" separately; and also because the periods of administration and non-administration of the mineralizing agent are "defined" or "controlled" by precise osteologic variables and therefore, are not fixed.

In other words, the present inventors have developed a new procedure for the treatment of Osteogenesis imperfecta and means for carrying out such treatment. This procedure consists in the first stage, of the administration of enough quantity of bisphosphonate preparation during the necessary period of time to acquire a degree of volumetric mineral density of the cortical tissue of application, within the normal range (average±1 Ds). Then the administration of the bisphosphonate preparation is interrupted in order to enable the development of the sectional momentum of inertia. The length of the second stage can be determined by means of a tomography. That is to say, that the periods of administration or non-administration of the mineralizing agent are defined or controlled by precise osteologic variables and therefore are not fixed. If during the second stage the cortical mineral density drops by 5–10% of the maximum value previously obtained, administration of bisphosphonate preparation should be resumed until the corresponding maximum adjusted value is reached again. The proposed procedure of a period with bisphosphonate followed by another period without the bisphosphonate agent improves re resistance, provided that the length of both periods is contributed by defined osteologic variables.

In the following the invention and its scientific background is further illustrated.

OI causes bone fractures and/or deformities because bones have less resistance to usually applied forces. Indeed, patients suffering from OI are less resistant to fans, lever efforts, accidental bumps, jumping and walking, or even to its own body weight in the more severe cases. Reduced resistance is originated by: 1) calcified tissue of defective quality 2) extremely poor development of bone macroarchitecture.

In addition, the defective quality of calcified material is caused by two variables: 1a) poor mineral acquisition (low bone volumetric density) and 1b) deficient internal distribution of calcified tissue (as a result of a modelling and remodelling process performed without an adequate spatial directionality).

The 1a) component of the disease is attributed to an identified genetic defect expressed by a defective synthesis of collagen fibres, which become inappropriate for mineral linkage and crystal growth. Instead components 1b and 2 are acquired defects mainly attributed to low bone stimulation (mostly by staining forces). Bone macro-(2) and microarchitecture (1b) is modelled and remodeled according to the individual requirements of bone mechanical uses. The best stimuli for bone architecture are the normal deformities (strains) daily applied to bones by external charges. These deformities are detected by cells located within the calcified matrix, the osteocytes, which through a complex chain of chemical mediators modulate the modelling and remodelling activity carried out by the surface bone cells, the osteoclasts and osteoblasts. The scarce muscular development in OI children is; an important cause for the wrong bone architectural orientation. Indeed, as bone resistance is the result of bone adaptation to muscular use, patients suffering from OI, who arc compelled to stay immobile and even to undergo bone orthopaedic fastening, cannot develop their muscles properly.

Some of our observations suggest that the most severe OI cases would also imply a poor interrelation muscle/bone, called by some authors 'a mechanostatic defect'. Same induces less acquisition of bone resistance by muscle unit. The weakened muscles are also unable to produce good bone architectural quality, compared to the efficiency of tee process in normal children. We named this qualitative mechanostatic defect 'type 3 defect', and its origin may also be genetic although it has not been identified yet.

Thus, bone fragility landscape in OI becomes quite complex if we consider the simultaneous existence of type 1a, 1b, 2 and 3 defects.

As in densitometric (x-ray absorptometry) studies these patients show bones less dense than normal ones, bisphosphonates' administration has been tried (particularly pamidronate and olpadronate) as palliative for OL.

Bisphophonates increase bone mineral density in OI, and although it has not been proved yet, they are claimed to reduce fracture rates. This known use derives from the application of bisphosphonates in the treatment of bone fragility in adults, as in the case of different types of osteoporosis (postmenopausal, senile, by corticosteroids, etc.).

Bisphosphonates are agents that inhibit bone resorption and thus delay the exchange process of calcified mass, increasing bone mineral density (probably they increase bone mass by occupying non calcified sites but not due to a true increase in mineral density). That is why these compounds are successfully used in the treatment of osteoporosis. Osteoporosis is an adult disease, characterized by a predisposition to suffer fractures due to fragility. With bisphosphonates % bone mass augments and there is a certain decrease in fractures. However, compared with OI, patients with osteoporosis are adults, with mature skeletons (already macrostructured) and they will probably suffer just one of the type 1b defects (augment of cortical pores, decreased number of trabeculae, etc.), while some of them could show type 3 problems.

It is understood that OI and osteoporosis defects are different and so results can not be extrapolated It means that the problems to deal with are different and OI should not be treated as if it were an infantile osteoporosis. Notwithstanding, up to the present bisphosphonates are assayed in the treatment of OI with the same method as with adult osteoporosis.

That is why a new method which adapts bisphosphonates' use to the physiopathological characterstics of OI patients is invented We call this new method 'controlled on-off' because it consists of a combination of bisphosphonates administration periods ('on') with others free of these agents ('off'). The 'on-off controlled' clearly differs from the bisphosphonates cyclic uses in that the latter are designed in fixed cycles (not controlled) and in that their goal is to discouple the function of bone surface cells in order to obtain a calcium positive balance. That is to say that during some time they inhibit osteoclast so as the osteoblast action prevails and so they are only useful to increase bone mineral density.

The 'on-off controlled' method in turn has the therapeutic purpose of improving bone architecture, independently from mineralization which can be normal or even decreased temporarily. The invent is characterized by the administration of certain bisphosphonates which present a period meant to, compensate the defect 1a ('on' stage), but in a way that is not intended to discouple the bone cellular fiction. To reach this goal we selected non-toxic bisphosphonates (preferably pamidronate, olpadronate and alendronate) which are administered in small daily doses (not in large cycles each time) with the aim of halting the restorptive metabolism and allowing osteoclasts and osteoblasts to reach a new balanced level of activity. Then the invented method proposes to continue with a period aimed to correct defect 1b and 2 ('off' stage) by releasing bisphosphonate stimuli (preferably those compounds whose effects are quickly reversible like pamidronate and olpadronate) The 'off' stage should be accompanied by physical activities to help the natural orientation or disposition of the calcified material previously obtained during the 'on' stage. In act, it is believed that this architectural orientation is not suitable with a poor mineralised tissue.

The concept that supports this method is that in OI children poor bone material hinders the possibility of getting advantage from the minimum mechanical stimuli sent out by their muscular activity. The material improvement obtained by using bisphosphonates opposes the remodelling action of muscular stimulus. Thus consecutive stages are to be taken, first to improve the material with bisphosphonates and then to improve architecture without bisphosphonates, but in a previously enhanced material.

The duration for each stage is not fixed (they arc not fixed cycles as the ones claimed by other methods) but delimited (controlled) by easily measurable osteologic variables. The 'on' stage lasts until bone mineral density (volumetric bone mineral density) reaches a normal range according to the age of the patient, or until a maximum effect is obtained (steady state). The 'off' stage goes from the end of the previous one until bone mineral density falls either below normal range or below 10% the maximum effect previously reached. Later on another 'on' stage takes place and so on The aim is to reproduce in these patients the mineral acquisition and bone resistance curve of normal children. Normal children show a quite balanced development regarding bone calcification and architectural modelling of their bones which allows them to gain resistance gradually (see FIG. 1). Only during periods of fast growth this model loses its balance in favour of an architectonic optimization.

Children with OI do not gain resistance and thus they continually suffer fractures (FIG. 5). The mineral gain obtained with bisphosphonates, as they are used currently, calcifies bones but hinders their architectural gain (see Roldan et al JPEM 1999, 12:555). Bisphosphonate opposes architectural remodelling while muscular stimulus is too weak to defeat the metabolic inhibition it causes. The above mentioned explains the failure of current methods.

The 'controlled on-off' method matches the needs of gaining calcification and architecture, though calcification may temporarily be lost. The improvement is based in that a second calcification period will be performed over a structure previously improved during the off period, and from then on successively.

The present invention refers to the development of a new procedure for medical use and consists in the administration of enough bisphosphonates quantities through different ways of enough quantity of bisphosphonate preparation during the necessary period of time to acquire a degree of cortical mineral density of the cortical tissue of application, within the normal range (average±1 Ds) according to the patient's age, or until reaching a plateau effect in the evolution curve of the osseous mineral density (stage WITH or of MINERALIZATION). At that moment the bisphosphonate administration has to be interrupted in order to enable the development of the sectional momentum of inertia according to the normal use or by scheduled physical exercising (stage WITHOUT or ARCHITECTURIZATION). The length of the second stage can be determined by radiologic means, preferably by tomography, and specifically with procedures that can determine bone stability to torsion or flexion or calculate the sectional momentum of inertia. If during this second stage, the cortical mineral density drops by 5–10% of the maximum value previously obtained, administration of bisphosphonate preparation should be resumed until the corresponding maximum adjusted value is reached again, adjusted to the patient's age or until reaching a new plateau and subsequently (see FIG. 1).

Other advantages of his procedure are that risks of bone adverse effects are minimized, costs are reduced, and patient and family acceptation is increased in view of the reduction of the patient's exposure to the mineralizing agent.

Among the different types of bisphosphonates, the pamidronate and olpadronate are the favorite bisphosphonates tol be used with this procedure as they have demonstrated not to affect the growth of cartilage (Brumsen C et al, Medicine 1997, 76). Due to their antiresorptive power, of moderate degree, enough quantities of molecules are administered each time, to ensure minimum absorption, unlike more powerful compounds the oral absorption of which may be dubious.

Other bisphosphonates that can be used with this procedure are the amino-pamidronate, amino-olpadronate (IG-9402), amino-alendronate, amino-etidronate (all included in the patent application PCT 97/02827, priority Oct. 7, 1995, the disclosure of which is incorporated herein by reference) and also the already known alendronate, neridronate, ibandronate, risedronate, tiludronate, etidronate, clodronate, incadronate and zolendronate.

Oral administration formulations are preferable due to the mild suppression of the osseous metabolism that is exercised by this way of administration. The oral route is also preferred instead of injectable as in the latter bisphosphonates are administered in large quantities (zolendronate, ibandronate are particularly ineffective and injectable uses of other bisphosphonates). The quantities preferred do not discouple the bone cellular system for a protracted period (pamidronate and olpadronate are preferred, and in second place alendronate and risedronate). Nevertheless, the intravenous treatments may be useful alternatives.

Liquid oral formulations are preferred specially when the bisphosphonates is dissolved in a soft capsule (like the one suggested in the patent of Espanolola SP, 2.034.877, priority Apr. 4, 1991, the disclosure of which is incorporated herein by reference).

Formulations with gastro-resistant coating are preferred to avoid the exposure of the bisphosphonates to the sensitive mucosae of the esophagus and the stomach.

A packet, a box with packages of combined presentation and multipackages, specially designed to justify the WITH —WITHOUT times of bisphosphonates administration are preferred to increase compliance and avoid prescription mistakes.

The procedures for the obtention of bisphosphonates and their salts are, for example, those described in the Argentine patents No 200.473 (priority Aug. 11, 1974) and 218.558 priority 13/06/1980) and the claim filed on 15/07/97 (P97 01 03155). The disclosure of all these documents is incorporated herein by reference.

BRIEF DESCRIPTION OF THE DRAWINGS

The invention is further illustrated by the figures attached hereto wherein:

FIG. 3 is another schematic representation of a system of coordinates that shows the relation between the age and the degree of cortical mineralization (vBMD) in the tibia, both in normal children and in children with Osteogenesis Imperfecta treated with pamidronate;

FIG. 4 is another schematic representation of a system of coordinates that shows the relation between age and the diaphysial stability evolution (SSIpolar) or resistance to deformation by torsion) in normal children and children with Osteogenesis Imperfecta;

EXAMPLES

DETAILED DESCRIPTION OF THE INVENTION

Results observed in-group children affected by Osteogenesis Imperfecta are included. Example 1 contains the original observation of the specific improvement of the cortical mineral density (external) associated to the absence of the endoestal-resorption (internal), effects achieved by the administration of bisphosphonates and Example 2 contains the original observation on how, once optimal mineralization conditions are reached, it is possible to promote and control the architectonic improvement of bone.

Example I

Specific Improvement of Cortical Mineral Density Administration of Bisphosphonates Four children with Osteogenesis Imperfecta type III and one type IV, aged two and fourteen at the beginning of is study (6 and 17 at the end of continuous exposure to bisphosphonate), and having suffered from 4 to 79 fractures in different parts of the skeleton, were treated with disodium pamidronate for 2.5–4 years, following the "continuous" type scheme. The doses were adjusted to the patient's condition with a mean of 3.5 mg/Kg of body weight/day by oral administration, or 20 mg per dose, every 3–6 months, by intravenous administration in one of the cases. During bisphosphonate administration, it was possible to verify the reduction of the osseous metabolic turnover, according to the decrease of the basal figures of the biochemical markers of osseous resorption (mainly urinary hydroxyproline/creatinine) and osseous formation (mainly of total serum alkaline phosphatase and osteocalcin). Subsequent determination of osseous absorptiometries indicated the progressive improvement of the total apparent mineral density of the lumbar vertebrae and the neck of the femur, reaching ranges inferior to the age mean± 2 DS.

Figure 1:
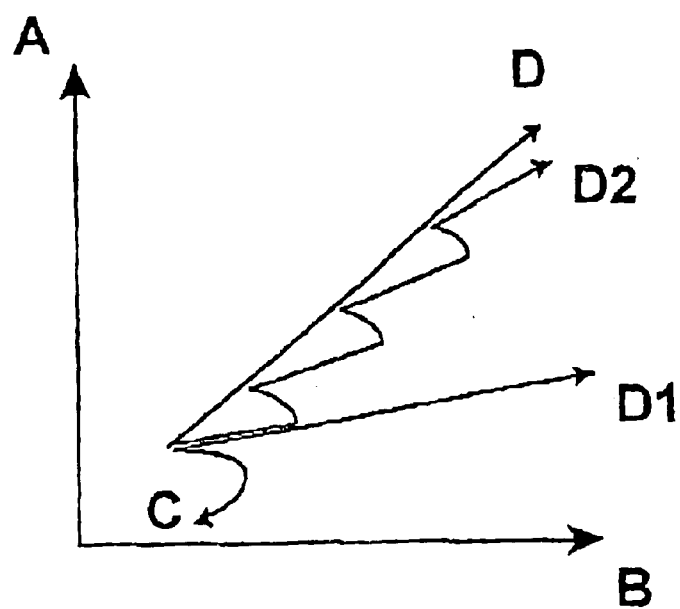
FIG. 1 is a schematic representation of a system of coordinates showing the relation between mineralization and architecture and the different results comparing the present procedure with already known ones.
Figure 2:
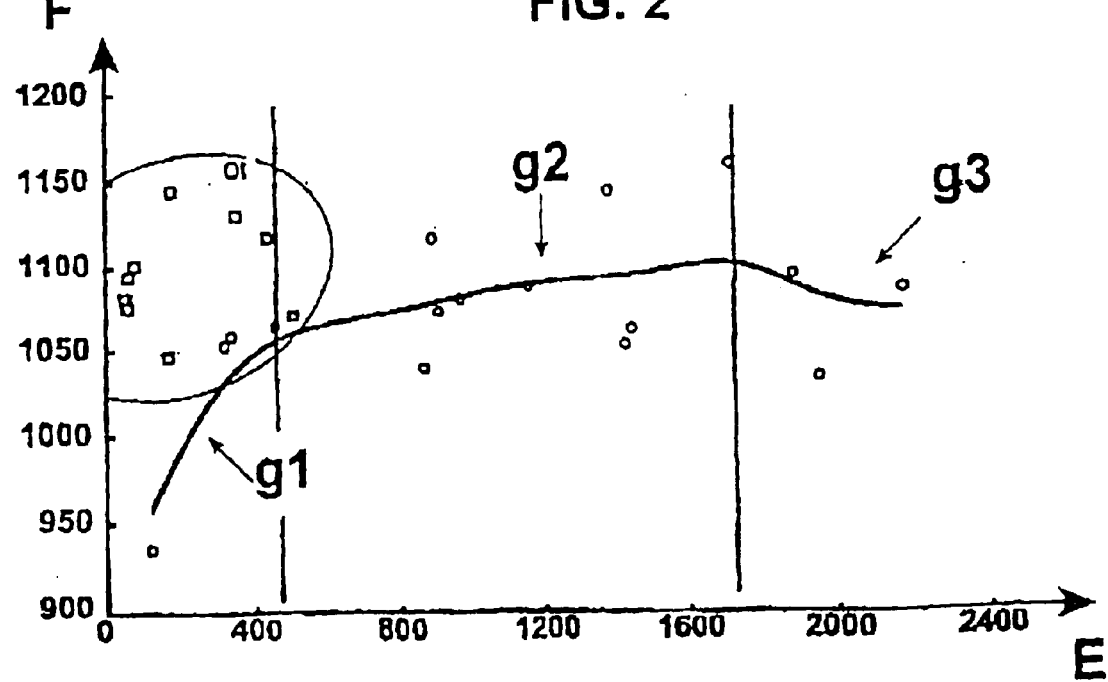
FIG. 2 is another schematic representation of a system of coordinates showing the relation between the cortical mineral density (vDMO) and the diaphysial stability of the tibia (SSIpolar) both in normal children and in children with Osteogenesis Imperfecta that were given bisphosphonates.
Figure 5:
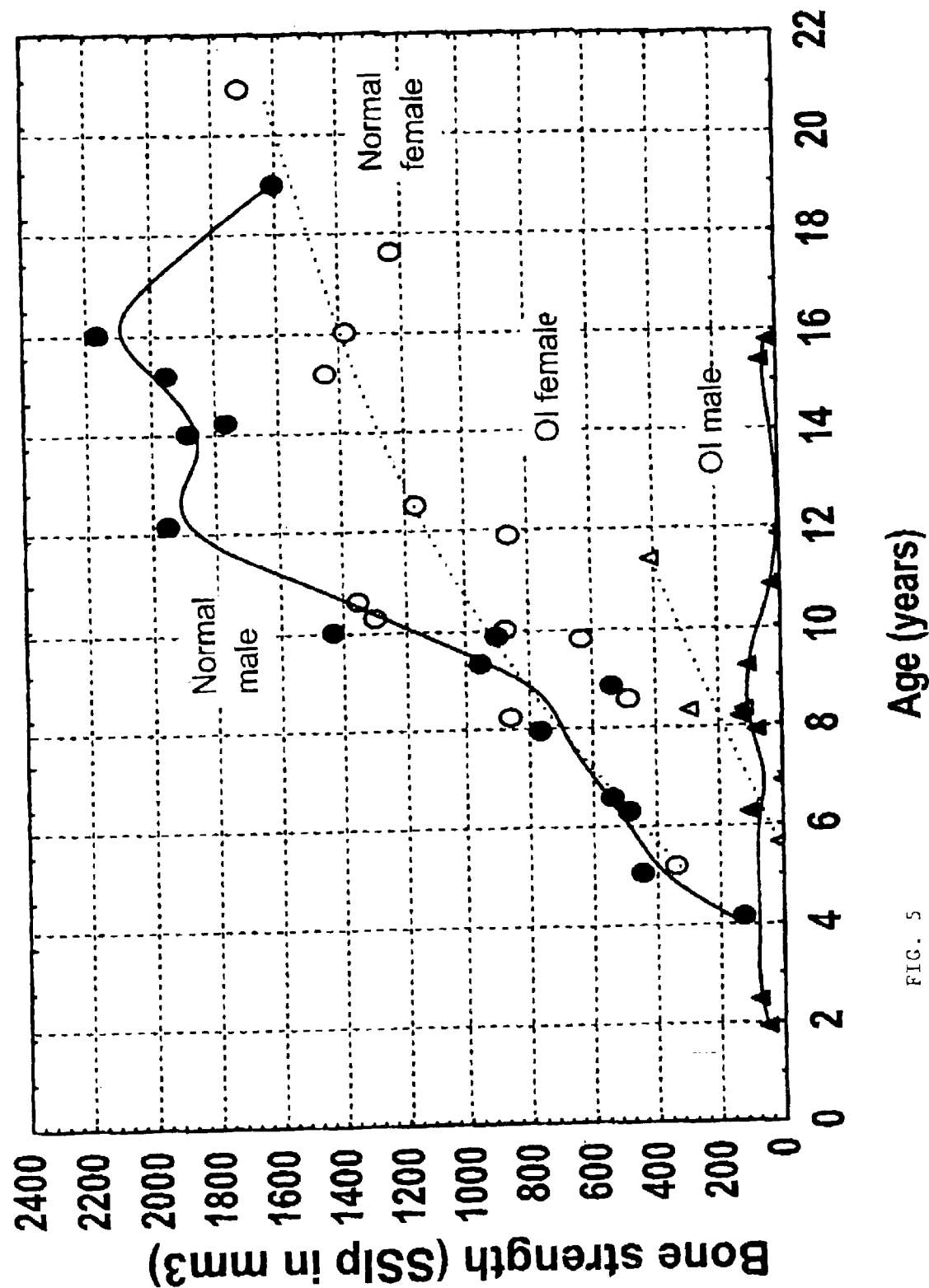
FIG. 5 shows the way in which 28 normal children acquire resistance compared to the failure at acquiring resistance by 14 untreated OI children. (Y axis) shows tibial resistance to strength assessed at each left calf through a tomographic index called the SSIp (strain-stress index at the polar axis) which represents the bone resistance to torque Cm mm3 of shearing). The SSIp is a combination of material (type 1) and architectonic (type 2) variables.
Figure 6:
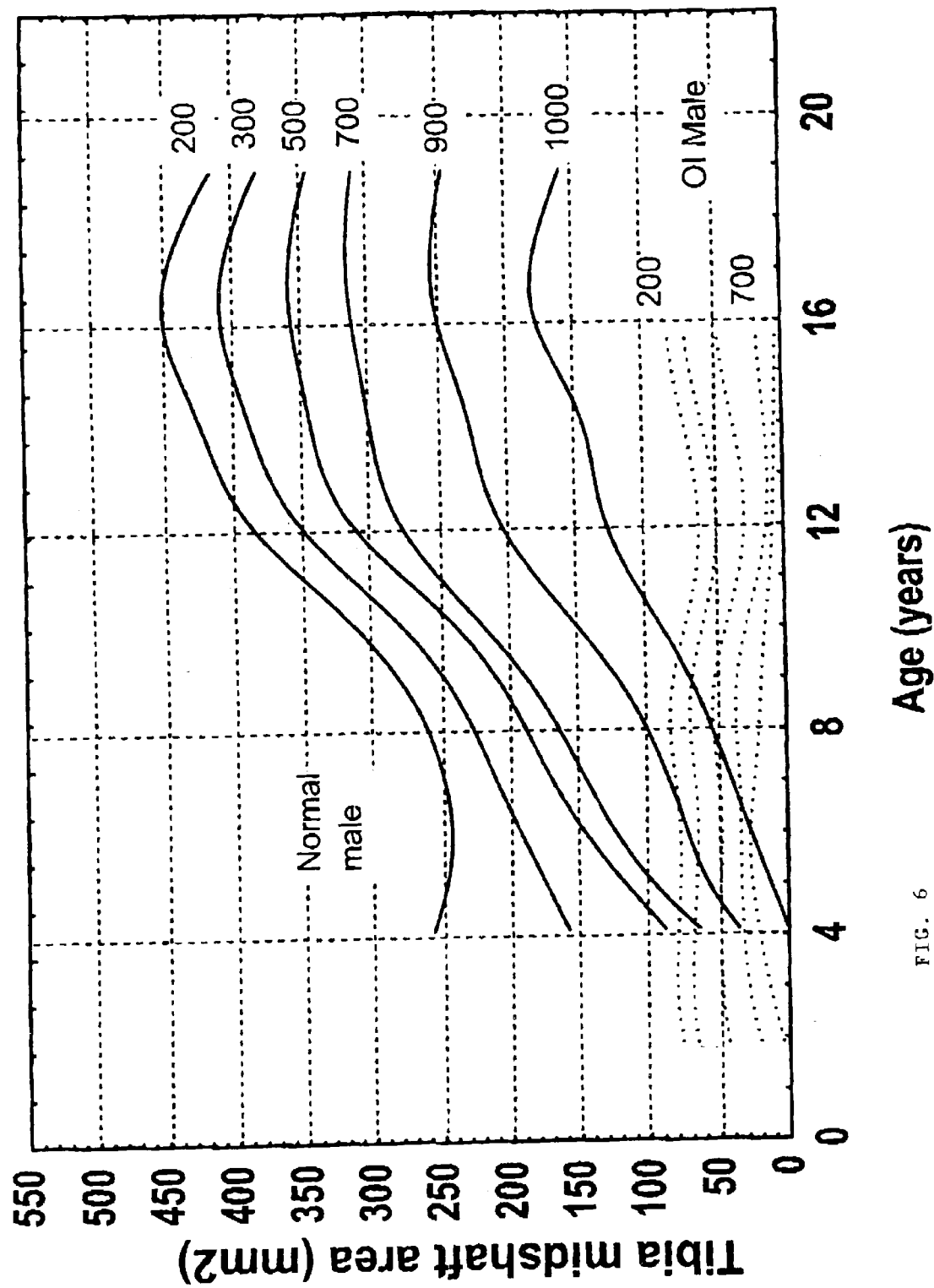
FIG. 6 compares the mean values of the tibia sectional area at midshaft, assessed by mineral density low thresholds (respectively of 200, 300, 500, 700, 900 and 100 mg) in 15 normal boys (solid lines) versus 10 untreated OI boys (dottedlines). It can be seen the lack of development of the bone sectional areas independently of the degree of mineral density.
Figure 7:
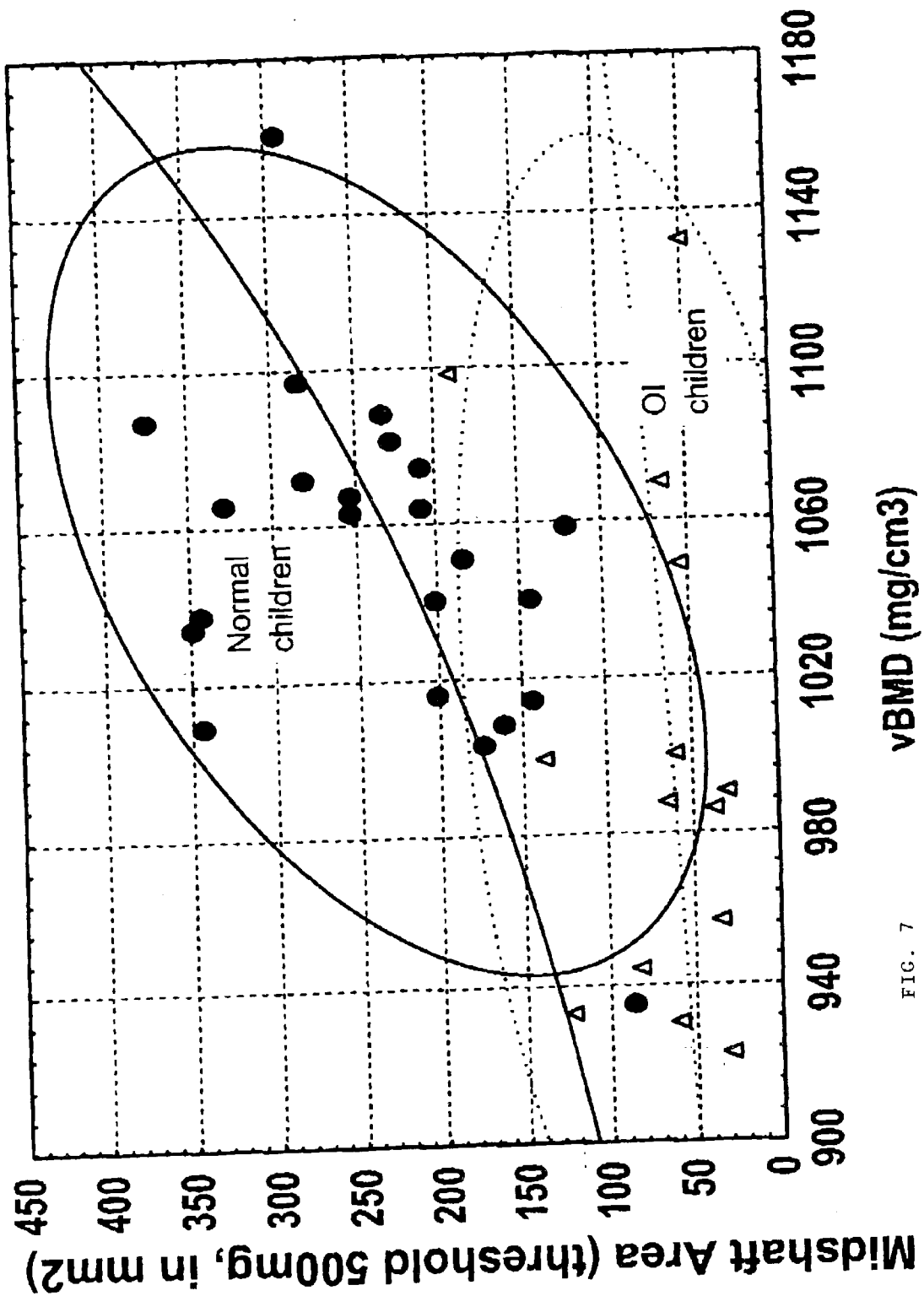
FIG. 7 compares the degree of mineral density (x axis; volumetric bone mineral density) versus the bone area sectional development (y axis) in 24 normal children (solid) versus 14 un-treated OI children (dotted), The picture shows the mineral density does not contribute to architecture development in OI children as in normal children. Then, such negative effect should be expected by administrating bisphosphonates to simply increase bone mineral density (current methods)
Figure 8:
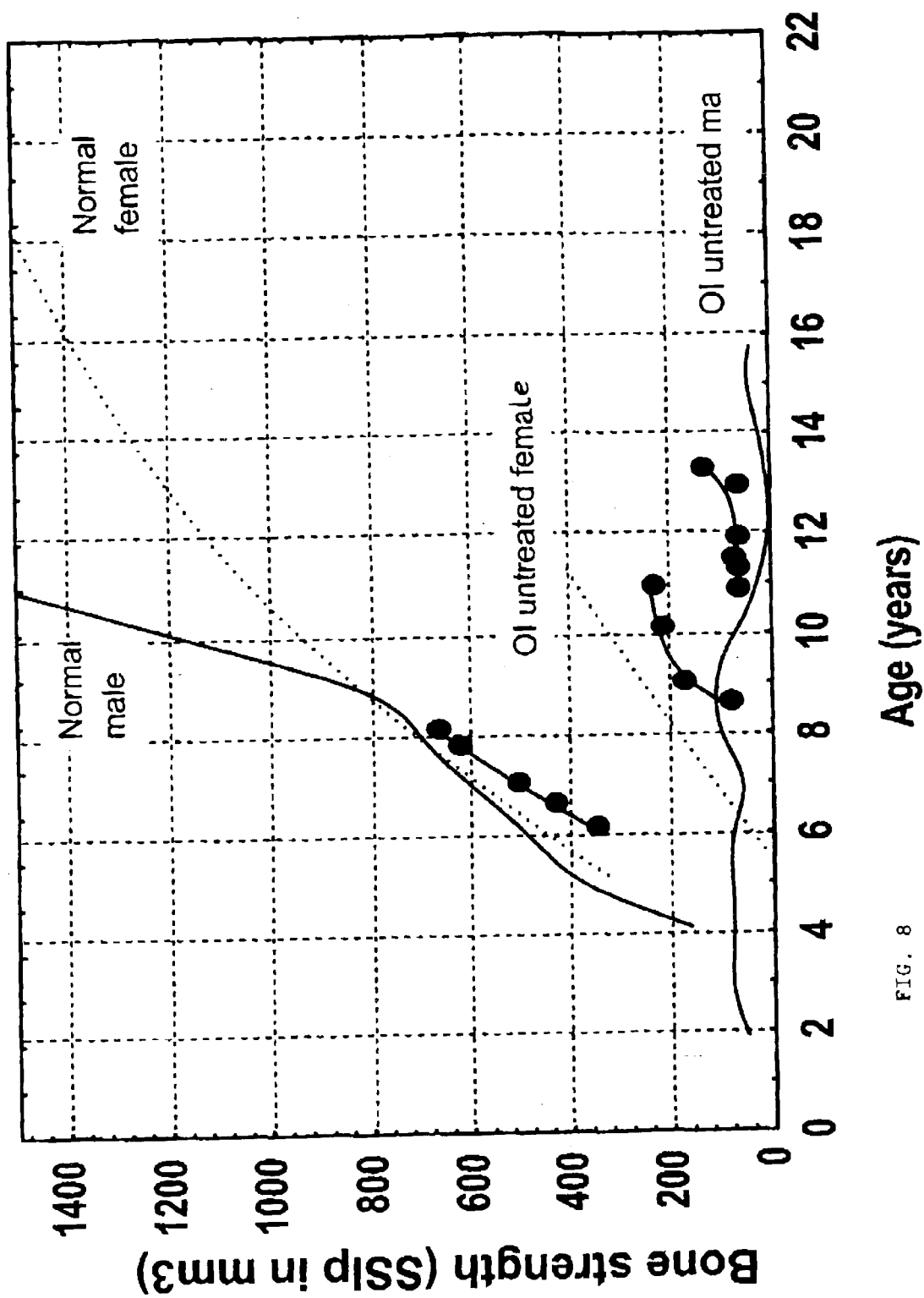
FIG. 8 repeats FIG. 5 but now including the evolution of 3 OI pamidronate treated children (black dots) under the 'on-off controlled' method.

The quantitative computerized tomography (system XCT 3000, Stratec) confirmed the proper degree of mineralization achieved specifically in the cortical type bone; but at the same time it showed a sub-cortical type of condensation in the endosteum, resulting in a low diaphysial stability, of about 8–10 times lower than that of normal children. The latter can be attributed to the scarce development of inertia due to the internal osseous lack of resorption in the diaphysis. In FIG. 2 it can be observed that in children with normal development, there exists a range of cortical mineralization which contributes to the diaphysial stability (resistance to deformation). This range is of approximately 1020–1100 mg/cm$^3$. The children with Osteogenesis Imperfecta treated with pamidronate have reached said mineralization range, but it does not help to improve diaphysial stability, due to the lack of architectonic development. In FIG. 3, it can be observed that the mineralization acquired in the cortical bone of children with Osteogenesis Imperfecta is similar to that of normal children of the same age.

The administration period of bisphosphonates was 2–4.5 years, indicating the existence of a wide interindividual variability in order to obtain the mineralizing effect and the inconvenience of adopting fixed periods of treatments.

The conclusion is that bisphosphonate is efficient to mineralize the osseous cortex, but that at the same time it contributes to the scarce architectural development of the diaphysis and therefore this procedure is incomplete and does not significantly improve resistance to fracture.

Example II

Specific Increase of Osseous Stability During the Period of Interruption in the Administration of Bisphosphonate.

The administration of bisphosphonates (cases A and B) was intended in two of the four children. In new tomographic exams, 4–11 months post-bisphosphonates the improvement in the stability rate is observed, despite a slight concomitant deterioration of the cortical mineralization (FIG. 4). This better index can only be obtained by the expansion of sectional momentum of inertia, as an expression of a better bone architecture. In fact, when the administration of bisphosphonate is interrupted, the endoestal mineral density decreases approximately 2–4% at 3–9 months, showing again a wide interindividual variation in the loss pace.

Consequently, the tomographic follow up is performed periodically in order to prevent that the osteopenia of the post-bisphosphonate cortical bone rises above 10% thus affecting the architectonic improvement achieved and indicating the convenience of a new period of "Mineralization" requirement. It can be concluded that the sequential procedure of a period of bisphosphonate followed by others without the antiresorptive agent improves fracture resistance provided that the length of both periods is controlled by defined osteologic variables.

The features of the present invention disclosed in the specification, the claims and/or the drawings may both separately and in any combination thereof be material for realizing the invention in various forms thereof.

Figure References:
A: Osseous architecture
B: Mineralization
C: Without treatment
D: Normal development
D1: Known mineralizing procedures
D2: New procedure
E: Diaphysial stability (SSI polar in mm3)
F: Cortical mineral density of the tibia (vDMO in mg/cm3)
G1: Moderate contribution
G2: High contribution
G3: Paradoxical contribution
H: Age (in years)
L: Norma men and women L1: Example of cases that discontinued pamidronate
L2; Example of cases that discontinued pamidronate
L3: Example of cases that continued with pamidronate
L4: Example of cases that continued with pamidronate
M: Tibia resistance to deformation by torsion or SSI polar (in mm3)
N1: Normal men
N2: Normal women
In FIG. 2:
○: normal children (n=13)
: children with Osteogenesis Imperfecta that were given bisphosphonates (n=4)
In FIG. 3:
○: normal children
•: children with Osteogenesis Imperfecta that were given pamidronate.
In FIG. 4:
○: Men
Δ: Women

What is claimed is:

1. A two-stage method for treating osteogenesis imperfecta, comprising:
   administering to a patient in need thereof a bisphosphonate in a first stage of treatment in order to obtain a predetermine bone volumetric mineral density;
   performing a bone volumetric mineral density test on said patient; and
   interrupting administration of the bisphophonate in a second stage of treatment in order to allow for architectonic expansion of the bone,
   wherein the predetermined bone volumetric mineral density is within the average range of the bone volumetric mineral density of a person±1 SD, said person of the same age as the patient under treatment,
   wherein the second stage ends when the bone volumetric mineral density falls below the average range of the bone volumetric mineral density of the person or below 10% of the bone volumetric mineral density material obtained at the end of the first stage.

2. The method of claim 1, further comprising determining the duration of the second stage by the development of the sectional momentum of inertia using radiologic means.

3. The method of claim 1, further comprising determining the duration of the second stage bone stability to torsion or flexion using tomography.

4. The method of claim 1, wherein the sectional momentum, of inertia of the person suffering from osteogenesis imperfecta to be treated matches the values of a person of the same age not suffering from Osteogenesis imperfecta.

5. The method of claim 1, further comprising determining at least one of the architectonic expansion of the bone, the bone stability to tension or flexion and bone volumetric mineral density by a method selected from the group comprising tomography and radiologic means.

6. The method of claim 1, further comprising adding a stage comprising administration of the bisphosphonates.

7. The method of claim 6, further comprising adding another stage comprising non-administration of the bisphosphonate.

8. The method of claim 7, further comprising adding at least one further stage, wherein the further stage comprises a first stage comprising administration of the bisphosphonate and a second stage comprising non-administration of the bishophonates.

9. The method of claim 1, further comprising selecting the bisphosphonate from the group consisting of pamidronate, olpadronate, amino-pamidronate, amino-olpadronate (IG 9402), amino-alendronate, amino-etidronate, alendronate, neridronate, ibandronate, risedronate, tiludronate, etidronate, clodronate, incadronate, zolendronate and mixtures of them.

10. The method of claim 9, wherein the bisphosphonate is pamidronate or olpadronate or a mixture of them.

11. The method of claim 1, wherein the bisphosphonate or mixture of bisphosphonate is a bisphosphonate preparation further comprising at least one compound selected from the group consisting of a pharmaceutically acceptable calcium salts, a pharmaceutically acceptable flour salts, vitamin D, Parathyroid hormone PTH, and fractions of PTH.

12. The method of claim 1, wherein the bisphosphonate is present in gastro-resistant formulations for oral administration.

13. The method of claim 1, further comprising administrating bisphosphonate at 25 to 300 mg daily doses.

14. The method of claim 1, wherein the bisphosphonate or the bisphosphonate comprising preparation is an injectable preparation, wherein the doses of bisphosphonate are about 5–60 mg for each administration at one-week to six-months intervals.

15. The method of claim 1, wherein the bisphosphonate is comprised in a preparation with the preparation being selected from the group consisting of tablets, capsules, solid forms, liquid soluble or suspension forms, gels and soft capsules.

16. A two-stage method for treating osteogenesis imperfecta comprising:
   administering to a patient in need thereof a bisphosphonate in a first stage of treatment in order to obtain a predetermine bone volumetric mineral density;
   performing a bone volumetric mineral density test on said patient; and
   interrupting administration of the bisphophonate in a second stage of treatment in order to allow for architectonic expansion of the bone,
   wherein the predetermined bone volumetric mineral density is within the average range of the bone volumetric mineral density of a person±1 SD, said person of the same age as the patient under treatment,
   wherein the second stage ends when the bone volumetric mineral density falls below the average range of the bone volumetric mineral density of the person or below 10% of the bone volumetric mineral density material obtained at the end of the first stage,
   wherein the bone volumetric mineral density is determined by measurement of sectional momentum of inertia.

* * * * *